(12) United States Patent
Zhou

(10) Patent No.: US 10,881,639 B2
(45) Date of Patent: Jan. 5, 2021

(54) USE OF COMPOSITION OF MULTIVITAMIN IN PREPARING DRUG FOR STIMULATING GASTROINTESTINAL SYSTEM MOTILITY

(71) Applicant: Zensun (Shanghai) Science & Technology, Co., Ltd., Shanghai (CN)

(72) Inventor: Mingdong Zhou, Shanghai (CN)

(73) Assignee: Zensun (Shanghai) Science & Technology, Co., Ltd., Shanghai (CN)

( * ) Notice: Subject to any disclaimer, the term of this patent is extended or adjusted under 35 U.S.C. 154(b) by 0 days.

(21) Appl. No.: 15/735,568

(22) PCT Filed: Jun. 6, 2016

(86) PCT No.: PCT/CN2016/084938
§ 371 (c)(1),
(2) Date: Dec. 11, 2017

(87) PCT Pub. No.: WO2016/197889
PCT Pub. Date: Dec. 15, 2016

(65) Prior Publication Data
US 2018/0353469 A1    Dec. 13, 2018

(30) Foreign Application Priority Data

Jun. 12, 2015 (CN) .......................... 2015 1 0321294

(51) Int. Cl.
| | |
|---|---|
| *A61K 31/375* | (2006.01) |
| *A61K 31/197* | (2006.01) |
| *A61K 31/4188* | (2006.01) |
| *A61K 31/4415* | (2006.01) |
| *A61K 31/455* | (2006.01) |
| *A61K 31/51* | (2006.01) |
| *A61K 31/525* | (2006.01) |
| *A61K 31/714* | (2006.01) |
| *A61K 31/519* | (2006.01) |
| *A61P 1/04* | (2006.01) |
| *A61P 1/10* | (2006.01) |
| *A23L 33/15* | (2016.01) |
| *A61P 1/14* | (2006.01) |

(52) U.S. Cl.
CPC ............ *A61K 31/375* (2013.01); *A23L 33/15* (2016.08); *A61K 31/197* (2013.01); *A61K 31/4188* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/714* (2013.01); *A61P 1/04* (2018.01); *A61P 1/10* (2018.01); *A61P 1/14* (2018.01); *A61K 2300/00* (2013.01)

(58) Field of Classification Search
CPC ................ A61K 31/197; A61K 31/375; A61K 31/4188; A61K 31/4415; A61K 31/455; A61K 31/51; A61K 31/519; A61K 31/525; A61K 31/714; A61P 1/04; A61P 1/10; A61P 1/14; A23L 33/15
See application file for complete search history.

(56) References Cited

U.S. PATENT DOCUMENTS

2003/0008016 A1* 1/2003 Crum ..................... A23C 9/206
424/535

FOREIGN PATENT DOCUMENTS

| CN | 104256652 A | | 1/2015 | |
|---|---|---|---|---|
| CN | 104337813 A | * | 2/2015 | ........... A61K 31/519 |
| WO | WO 2006/108208 A1 | | 10/2006 | |
| WO | WO 2012/012682 A2 | | 1/2012 | |
| WO | WO 2015/010449 A1 | | 1/2015 | |
| WO | WO-2015010449 A1 | * | 1/2015 | ............. A61K 31/51 |

OTHER PUBLICATIONS

Google machine translation of WO2015010449A1, https://patents.google.com, accessed online on Feb. 6, 2019. (Year: 2019).*
Malloy, H.R., J. Natl. Med. Assoc., 1950, p. 140-146 (Year: 1950).*

* cited by examiner

*Primary Examiner* — Jonathan S Lau
(74) *Attorney, Agent, or Firm* — Jones Day

(57) ABSTRACT

The present invention relates to a composition of multivitamin vitamin B-C, particularly a composition of vitamin B-C for stimulating gastrointestinal (GI) system motility. The composition is suitable for preventing and/or treating conditions or diseases associated with insufficient GI motility.

12 Claims, 4 Drawing Sheets

USE OF COMPOSITION OF MULTIVITAMIN IN PREPARING DRUG FOR STIMULATING GASTROINTESTINAL SYSTEM MOTILITY

This application is a national stage application of International Patent Application No. PCT/CN2016/084938, filed Jun. 6, 2016, which claims priority to Chinese application No. CN201510321294.2, filed Jun. 12, 2015, the disclosures of each of which are hereby incorporated by reference in their entirety.

FIELD OF THE INVENTION

The present invention relates to a composition comprising B vitamins and C vitamins, in particular to a composition comprising B vitamins and C vitamins for promoting motility of the gastrointestinal system. The present composition is suitable for the prevention and/or treatment of conditions or diseases associated with deficiencies of gastrointestinal motility.

BACKGROUND OF THE INVENTION

Nowadays, the pressure of people's life is generally increasing, the pace of life is accelerating, and the competition is fiercer day by day. More and more patients are suffering from gastrointestinal disorders or gastrointestinal discomfort. The pathogeny thereof is extensive, and the symptoms thereof are also different.

Gastrointestinal (GI) motility is a coordinated neuromuscular process that transports nutrients through the digestive system. Impaired motility of the gastrointestinal system can be involved in gastroesophageal reflux disease, gastroparesis (e.g., diabetic and postsurgical gastroparesis), irritable bowel syndrome (IBS), ileus, and constipation (e.g., functional or drug-induced constipation), and is one of the largest health care burdens of industrialized nations. In view of the above, a way to effectively stimulate motility of the gastrointestinal system is highly desirable and would be an advance in the art.

Functional dyspepsia and chronic gastritis often have such symptoms as abdominal fullness, upper abdominal pain, nausea, anorexia and so on. An important reason for this kind of symptoms is delayed gastric emptying caused by gastrointestinal motility disorders. And gastrointestinal motility disorders tend to cause IBS. Currently, drugs for treatment of gastrointestinal motility include metoclopramide, domperidone and itopride.

In the past, there were many kinds of drugs for treatment of gastrointestinal diseases, but few drugs have good curative effects and no side effects, and drugs or health care products with long-term health care effects as well as improving gastrointestinal function, promoting gastrointestinal motility and relieving gastrointestinal discomfort symptoms are even rare.

As mentioned above, (1) metoclopramide as a dopamine receptor blocking drug with strong central anti-vomiting and gastrointestinal tract excitement effects, can inhibit the relaxation of gastric smooth muscle, increase the response of gastrointestinal smooth muscle to cholinergic, accelerate gastric emptying, and increase the activity of the gastric antrum. In addition, the drug also has the function of stimulating the release of prolactin. The side effects of Metoclopramide commonly include lethargy, irritability, fatigue, and weakness. Moreover, high-dose or long-term use of the drug may block the dopamine receptor, showing the symptoms of Parkinson's disease. (2) Domperidone as a peripheral dopamine receptor antagonist can promote upper gastrointestinal peristalsis and tension recovery, facilitate gastric emptying, increase the movement of gastric antrum and duodenum, coordinate pyloric contraction, and enhance esophageal peristalsis and the tension of the lower esophageal sphincter. Because of its poor penetration into the blood brain barrier, domperidone almost has no antagonistic effect on the dopamine receptor in the brain. It is reported abroad that its high-dose intravenous injection may cause seizures (there is no this preparation in China). This drug, however, is a powerful prolactin-releasing drug which may cause menstrual disorders. (3) Itopride has dual effects of dopamine receptor blockade and acetylcholinesterase inhibition. It can enhance the movement of stomach and duodenum and facilitate gastric emptying by stimulating the release of endogenous acetylcholine and inhibiting the hydrolysis thereof. It also has a moderate anti-vomiting effect. The elderly or aged patients should use this drug with caution.

B vitamins are all water soluble, most of which are coenzymes, taking part in the in vivo metabolism of sugar, protein and fat.

Vitamin B1 (thiamine) can promote gastrointestinal peristalsis and increase appetite. Vitamin B1 can inhibit the activity of cholinesterase to hydrolyze acetylcholine. Lack of vitamin B1 may increase the activity of cholinesterase and accelerate the hydrolysis of acetylcholine. Acetylcholine is an important neurotransmitter and its deficiency can lead to nerve conduction disorders, especially affecting the nerve conduction at the gastrointestinal tract and gland, and lead to slow gastrointestinal peristalsis, abdominal distension, diminished digestive glandular secretion, and appetite decrease.

Vitamin B2 constitutes many important coenzymes in the flavoproteins. It can be converted into flavin mononucleotide (FMN) and flavin adenine dinucleotide (FAD), both of which are important coenzymes in the tissue respiration, function to transfer hydrogen in the enzyme system, and participate in the metabolism of sugar, protein and fat, and can maintain normal visual function. Furthermore, Vitamin B2 can activate Vitamin B6 and convert tryptophan into niacin, and may be related to maintaining the integrity of red blood cells. It can maintain and improve the health of epithelial tissue, such as the gastrointestinal mucosal tissue. When the human body lacks B2, especially in severe deficiency status, the mucosal layer of human body cavity will have problems that cause mucosal lesions, and this can enhance the carcinogenic effect of chemical carcinogens. Vitamin B2 can thus prevent cancer.

Vitamin B3 (niacin) constitutes a coenzyme of dehydrogenase in the body. Vitamin B3, as the most requisite amount of B vitamins of the human body, not only keeps health of the digestive system, but also alleviates gastrointestinal disorders. Niacin is converted into nicotinamide in the human body. Nicotinamide is a component of coenzyme I and coenzyme II and participates in the in vivo lipid metabolism, oxidation process of tissue respiration, and the anaerobic decomposition of carbohydrates. It can keep the health of the digestive system, relieve gastrointestinal disorders, and effectively relieve the symptoms of constipation. Its deficiency can lead to angular cheilitis, glossitis, diarrhea, and so on. Diarrhea is a typical symptom of this disease. Constipation often occurs in its early days. Then it is often accompanied by diarrhea because of enteritis and the atrophy of the intestinal wall, digestive gland, intestinal wall and mucosa, and intestinal villus. The stool is watery or pasty, with large quantities and a lot of stink and sometimes with blood. Tenesmus may happen when the lesion is near the anus. Diarrhea is often severe and refractory and can be combined with absorption disorders.

Vitamin B5 (pantothenic acid) has an active form of coenzyme A, is an acyl carrier in vivo, and participates in the metabolism of sugar, fat, and protein. They work synergistically to regulate metabolism, maintain skin and muscle health, enhance the functions of the immune system and nervous system, and promote cell growth and division (including promotion of production of red blood cells and prevention of anemia). The lack of vitamin B5 may lead to the symptoms including anepithymia, dyspepsia, and being susceptible to duodenal ulcer.

Vitamin B6 comprises pyridoxine, pyridoxal and pyridoxamine, which can be transformed to one another. It can react with ATP in vivo via an enzyme and then be transformed into a coenzyme of a variety of enzymes having physiological activity, thereby participating in various metabolic functions of amino acids and fats. Combined with vitamin B1, it has a strong analgesic effect. Vitamin B12 can enhance the analgesic effect by the combination of the above two, and relieve the pain caused by peripheral nerve disease and spinal cord disease. Studies have reported that the intravenous drip of vitamin B6 mixed with azithromycin can reduce side effects of azithromycin on the gastrointestinal tract. Its main targets are blood, muscle, nerves, skin, etc. Its functions are the synthesis of antibodies, production of gastric acid in the digestive system, utilization of fat and protein (which should be supplemented especially on a diet), and the maintenance of the sodium/potassium balance (stabilization of the nervous system). Lack of vitamin B6 damages cells and affect humoral immunity. Feeding of vitamin B6 can improve immunity, reduce carcinogens in the body, and has a certain anticancer effect.

Vitamin B7, also known as vitamin H, biotin, and coenzyme R, is involved in the metabolism of fatty acids and carbohydrates in the body, promoting protein synthesis. It also involved in the metabolism of vitamin B12, folic acid, and pantothenic acid. It can promote urea synthesis and excretion, enhance the body's immune response and resistance to infection, stabilize the lysosomal membrane of normal tissues, maintain the body's humoral immunity and cellular immunity, affect the secretion of a series of cytokines, improve the body's immune function, and reduce the symptoms of perianal eczema and itching. The biotin side chain carboxyl group can be linked to the lysine residues of the enzyme via an amide bond. Biotin is a carboxyl carrier and is also involved in the metabolism of vitamin B12, folic acid, and pantothenic acid.

Vitamin B9 (folic acid) belongs to water-soluble B vitamins consisting of pteridine, p-aminobenzoic acid, and glutamic acid residues. The drug is absorbed by the intestinal tract and then passes through the portal vein into the liver, where it is converted into an active tetrahydrofolic acid under the action of the dihydrofolate reductase. Tetrahydrofolic acid is the carrier of "one carbon group" in the body. The "one carbon group" can be linked to the tetrahydrofolic acid at its 5 or 10-position carbon atom, and is mainly involved in the synthesis and transformation of purine nucleotides and pyrimidine nucleotides. The methyl group required for conversion of uracil nucleotides to thymidine nucleotides is derived from the methylene group provided by tetrahydrofolic acid bearing a "one carbon group". As a result, folic acid deficiency can result in a "one carbon group" transfer barrier, and a difficult synthesis of thymidine nucleotide, thereby affecting DNA synthesis and slowing down the rate of cell division, that is, the cell cycle will only stay in the G1 phase and the S and G2 phases will be relatively prolonged. The above changes will affect not only hematopoietic cells (causing the megaloblastic anemia) but also the somatic cells (especially the digestive tract mucosal cells). Folic acid deficiency can lead to B1 absorption disorders. The health benefits of folic acid for women are widely noted in the medical community, and pregnant and lactating women should be supplemented with folic acid. Besides, it can be used to prevent rectal cancer and heart disease. It has also been found to prevent free radicals from destroying chromosomes. Humans with deficient folic acid may suffer from megaloblastic anemia and leukopenia.

Deoxyadenosine cobalamin is the main existing form of vitamin B12 in the body and is a cobalt-containing red compound that is active only after it is converted to methylcobalamin and coenzyme B12. Vitamin B12 and folic acid play an important role in DNA synthesis. In addition, vitamin B12 also plays an important role in the maturation of red blood cells and in the normal maintenance of the nervous system. It is often associated with the role of folic acid. Folic acid has multiple coenzyme forms in the cell, and some studies have suggested that folic acid can intervene in the occurrence of gastrointestinal cancer and that folic acid can treat atrophic gastritis and improve gastric mucosal pathology.

Choline bitartrate has the effect of promoting the transformation of phospholipids and accelerating the operation of fat, and has a cholagogic effect; inositol can promote cell metabolism, promote development, and increase appetite. P-aminobenzoic acid (PABA) is actually a component of folic acid and it functions as a coenzyme in the body. PABA works with folic acid to promote protein metabolism and blood cell production.

Vitamin C, also known as ascorbic acid, is one of antioxidant vitamins. It participates in hydroxylation reaction in the body and is required for the formation of bones, teeth, and the interstitial adhesions in connective tissues and non-epithelial tissues. It can maintain the normal function of the teeth, bones, and blood vessels, and increase resistance to diseases. It is reported that vitamin C is deficient at different levels in various populations. When the body has some small problems, people should promptly be supplemented with vitamins and minerals to improve nutrition deficiencies, especially the elderly should pay more attention. Vitamins have a preventive effect on many diseases, many diseases may be more or less related to the lack of vitamin C, and vitamin C can also be combined with many other drugs to treat some diseases. Vitamin C is an antioxidant that protects the body from the threat of free redicals. Vitamin C is also a coenzyme. Many studies have shown that vitamin C can block the synthesis of carcinogenic N-nitroso compounds, prevent the formation of carcinogenic ammonium nitrate in the salted, pickled, and smoked foods containing nitrite (bacon, sausage, and so on), and prevent cancer, especially it has a better preventive effect on rectal cancer and colon cancer. At the same time, it has the effect of softening the blood vessels of the anus and increasing the elasticity of the anus. VC is easily damaged by heat or oxidants, especially light, trace heavy metals, and fluorescent substances can promote its oxidation, which makes VC be greatly restricted in application. Therefore, derivatives of vitamin C, including metal salts of VC, esters generated by VC with various acids, and compounds of VC and carbohydrates, etc., not only can get rid of the instability nature of VC, but also can better exert the physiological function of VC. These derivatives include vitamin C (L-ascorbic acid), Sodium ascorbate (L-sodium ascorbate), magnesium ascorbyl phosphate, L-Ascorbate-polyphosphate, ascorbyl palmitate, ascorbin stearate, vitamin C and glucose compound, etc.

From the perspective of mechanism of action, vitamin B is an important coenzyme involved in energy metabolism of human body, and vitamin C can promote the body's absorption of members of B vitamins. Multivitamin B C is used to improve the energy metabolism of the human body and provide more energy for the gastrointestinal tract to improve the functional dyspepsia caused by inadequate gastrointestinal motility. The mechanism for the increase in energy metabolism includes assisting carbohydrates and fat in releasing energy, decomposing amino acids, and transporting nutrient-containing oxygen and energy throughout the body. Multivitamin BC will be likely to become a new drug or health food with higher safety for promoting the motility of gastrointestinal system, yet there is no evidence to date to prove the ability of vitamin B and vitamin C to promote the motility of the gastrointestinal system, especially the therapeutic and regulatory effect of vitamin B and vitamin C on motility disorders of the gastrointestinal system in pathological state. Due to the large number of family members of B vitamins and their interdependent relationship, component selection and compatibility of the B vitamins are very important for preparation of drugs or health food for the treatment or regulation of motility disorders of the gastrointestinal system.

DISCLOSURE OF THE INVENTION

The present invention relates to a method of stimulating the motility of the gastrointestinal system in a subject in need thereof, wherein said subject suffers from diseases (i.e., disorders, conditions, symptoms, or drug- or surgery-induced dysfunction) of the gastrointestinal system. The method comprises administering to a subject in need thereof a therapeutically effective amount of a composition comprising B vitamins and C vitamins. The vitamins referred to in this invention comprise their corresponding analogues or derivatives, for example, vitamin B1 means thiamine and analogs or derivatives thereof, vitamin B2 denotes riboflavin and analogs or derivatives thereof; vitamin B3 refers to nicotinic acid and analogs or derivatives thereof; vitamin B5 means pantothenic acid and analogs or derivatives thereof; vitamin B6 means pyridoxine and analogs or derivatives thereof; vitamin B7 is biotin and analogues or derivatives thereof; vitamin B9 means folic acid and analogs or derivatives thereof, vitamin B12 means cyanocobalamine and analogs or derivatives thereof; vitamin C means ascorbic acid and analogs or derivatives thereof; and so on. In one preferred embodiment, the composition comprising B vitamins and C vitamins is a composition comprising vitamin B1 (thiamine), vitamin B2 (riboflavin), vitamin B3 (nicotinic acid), vitamin B5 (pantothenic acid), vitamin B6, biotin, and vitamin C. In one more preferred embodiment, the composition comprising B vitamins and C vitamins is a composition comprising vitamin B1 (thiamine), vitamin B2 (riboflavin), vitamin B3 (nicotinic acid), vitamin B5 (pantothenic acid), vitamin B6, folic acid, biotin, vitamin C, choline bitartrate, and inositol. In another more preferred embodiment, the composition comprising B vitamins and C vitamins is a composition comprising vitamin B1 (thiamine), vitamin B2 (riboflavin), vitamin B3 (niacin), vitamin B5 (pantothenic acid), vitamin B6, vitamin B12, folic acid, biotin, vitamin C, choline bitartrate, inositol, and p-aminobenzoic acid.

In another aspect, this invention provides a composition comprising an effective amount of a combination of B vitamins and C vitamins, and a pharmaceutically acceptable carrier. In one preferred embodiment, the composition comprises an effective amount of vitamin B1 (thiamine), vitamin B2 (riboflavin), vitamin B3 (niacin), vitamin B5 (pantothenic acid), vitamin B6, biotin, and a pharmaceutically acceptable carrier. In one more preferred embodiment, the composition comprises an effective amount of vitamin B1 (thiamine), vitamin B2 (riboflavin), vitamin B3 (niacin), vitamin B5 (pantothenic acid), vitamin B6, folic acid, biotin, vitamin C, choline bitartrate, inositol, and a pharmaceutically acceptable carrier. In another more preferred embodiment, the composition comprises an effective amount of vitamin B1 (thiamine), vitamin B2 (riboflavin), vitamin B3 (niacin), vitamin B5 (pantothenic acid), vitamin B6, vitamin B12, folic acid, biotin, vitamin C, choline bitartrate, inositol, p-aminobenzoic acid, and a pharmaceutically acceptable carrier.

In yet another aspect, the present invention relates to a composition comprising an effective amount of a combination of B vitamins and C vitamins, and an effective amount of drugs for treating and/or preventing gastrointestinal diseases. In one preferred embodiment, the composition comprises an effective amount of vitamin B1 (thiamine), vitamin B2 (riboflavin), vitamin B3 (niacin), vitamin B5 (pantothenic acid), vitamin B6, biotin, vitamin C, and an effective amount of drugs for treating and/or preventing gastrointestinal diseases. In one more preferred embodiment, the composition comprises an effective amount of vitamin B1 (thiamine), vitamin B2 (riboflavin), vitamin B3 (niacin), vitamin B5 (pantothenic acid), vitamin B6, folic acid, biotin, vitamin C, choline bitartrate, inositol, and an effective amount of drugs for treating and/or preventing gastrointestinal diseases. In another more preferred embodiment, the composition comprises an effective amount of vitamin B1 (thiamine), vitamin B2 (riboflavin), vitamin B3 (niacin), vitamin B5 (pantothenic acid), vitamin B6, vitamin B12, folic acid, biotin, vitamins C, choline bitartrate, inositol, p-aminobenzoic acid, and an effective amount of drugs for treating and/or preventing gastrointestinal diseases.

In still yet another aspect, the present invention relates to a composition comprising an effective amount of a combination of B vitamins and C vitamins, and an effective amount of other vitamin compounds. In one preferred embodiment, the composition comprises an effective amount of vitamin B1 (thiamine), vitamin B2 (riboflavin), vitamin B3 (niacin), vitamin B5 (pantothenic acid), vitamin B6, biotin, vitamin C, and an effective amount of other vitamin compounds. In one more preferred embodiment, the composition comprises an effective amount of vitamin B1 (thiamine), vitamin B2 (riboflavin), vitamin B3 (niacin), vitamin B5 (pantothenic acid), vitamin B6, folic acid, biotin, vitamin C, choline bitartrate, inositol, and an effective amount of other vitamin compounds. In another more preferred embodiment, the composition comprises an effective amount of vitamin B1 (thiamine), vitamin B2 (riboflavin), vitamin B3 (niacin), vitamin B5 (pantothenic acid), vitamin B6, vitamin B12, folic acid, biotin, vitamin C, choline bitartrate, inositol, p-aminobenzoic acid, and an effective amount of other vitamin compounds. The other vitamin compounds include vitamin A, vitamin D, vitamin E, vitamin K compounds and the like.

Promotion of gastrointestinal motility is used in a method for the treatment of drug-induced gastrointestinal dysfunction (e.g., opioid-induced, such as morphine-induced intestinal dysfunction or constipation) in an object in need thereof. The method comprises administering a therapeutically effective amount of a combination of B vitamins and C vitamins. Said object can be using opioid substances or opioids for post-surgical pain control or chronic pain control. Examples of opioid substances and opioids include morphine, codeine, oxycodone, hydrocodone, methadone, fentanyl, and the combination thereof with an anti-inflammatory agent (such as acetaminophen or aspirin). In one preferred embodiment, the composition comprising B vitamins and C vitamins is a composition comprising vitamin B1 (thiamine), vitamin B2 (riboflavin), vitamin B3 (niacin), vitamin B5 (pantothenic acid), vitamin B6, biotin, and vitamin C. In one more preferred embodiment, the composition comprising B vitamins and C vitamins is a composition comprising vitamin B1 (thiamine), vitamin B2 (riboflavin), vitamin B3 (niacin), vitamin B5 (pantothenic acid), vitamin B6, folic acid, biotin, vitamin C, choline bitartrate, and inositol. In another more preferred embodiment, the composition comprising B vitamins and C vitamins is a composition comprising vitamin B1 (thiamine), vitamin B2 (riboflavin), vitamin B3 (niacin), vitamin B5 (pantothenic acid), vitamin B6, vitamin B12, folic acid, biotin, vitamin C, choline bitartrate, inositol, and p-aminobenzoic acid.

The promotion of gastrointestinal motility can be used to treat gastroparesis in an object in need thereof by administering a therapeutically effective amount of a combination of B vitamins and C vitamins. In one preferred embodiment, the composition comprising B vitamins and C vitamins is a composition comprising vitamin B1 (thiamine), vitamin B2 (riboflavin), vitamin B3 (niacin), vitamin B5 (pantothenic acid), vitamin B6, biotin, and vitamin C. In one more preferred embodiment, the composition comprising B vitamins and C vitamins is a composition comprising vitamin B1 (thiamine), vitamin B2 (riboflavin), vitamin B3 (niacin), vitamin B5 (pantothenic acid), vitamin B6, folic acid, biotin, vitamin C, choline bitartrate, and inositol. In another more preferred embodiment, the composition comprising B vitamins and C vitamins is a composition comprising vitamin B1 (thiamine), vitamin B2 (riboflavin), vitamin B3 (niacin), vitamin B5 (pantothenic acid), vitamin B6, vitamin B12, folic acid, biotin, vitamin C, choline bitartrate, inositol, and p-aminobenzoic acid.

In another embodiment, the promotion of gastrointestinal motility is used in a method for the treatment of a gastro esophageal reflux disease (GERD) in an object in need thereof. The method comprises administering a therapeutically effective amount of a combination of B vitamins and C vitamins. In one preferred embodiment, the composition comprising B vitamins and C vitamins is a composition comprising vitamin B1 (thiamine), vitamin B2 (riboflavin), vitamin B3 (niacin), vitamin B5 (pantothenic acid), vitamin B6, biotin, and vitamin C. In one more preferred embodiment, the composition comprising B vitamins and C vitamins is a composition comprising vitamin B1 (thiamine), vitamin B2 (riboflavin), vitamin B3 (niacin), vitamin B5 (pantothenic acid), vitamin B6, folic acid, biotin, vitamin C, choline bitartrate, and inositol. In another more preferred embodiment, the composition comprising B vitamins and C vitamins is a composition comprising vitamin B1 (thiamine), vitamin B2 (riboflavin), vitamin B3 (niacin), vitamin B5 (pantothenic acid), vitamin B6, vitamin B12, folic acid, biotin, vitamin C, choline bitartrate, inositol, and p-aminobenzoic acid. In a specific embodiment, said gastro esophageal reflux disease is nighttime gastro esophageal reflux disease.

The invention also provides a method of promoting gastrointestinal motility to treat the irritable bowel syndrome (IBS) in an object in need thereof by administering a therapeutically effective amount of a combination of B vitamins and C vitamins. In one preferred embodiment, the composition comprising B vitamins and C vitamins is a composition comprising vitamin B1 (thiamine), vitamin B2 (riboflavin), vitamin B3, vitamin B5 (pantothenic acid), vitamin B6, biotin, and vitamin C. In one more preferred embodiment, the composition comprising B vitamins and C vitamins is a composition comprising vitamins B1 (thiamine), vitamin B2 (riboflavin), vitamin B3 (niacin), vitamin B5 (pantothenic acid), vitamin B6, folic acid, biotin, vitamin C, choline bitartrate, and inositol. In another more preferred embodiment, the composition comprising B vitamins and C vitamins is a composition comprising vitamin B1 (thiamine), vitamin B2 (riboflavin), vitamin B3 (niacin), vitamin B5 (pantothenic acid), vitamin B6, vitamin B12, folic acid, biotin, vitamin C, choline bitartrate, inositol, and para-aminobenzoic acid. Said irritable bowel syndrome can be either a constipation-type irritable bowel syndrome or a constipation-and-diarrhea-alternating-type irritable bowel syndrome.

The invention also provides a method for treating constipation by promoting gastrointestinal motility in an object in need thereof by administering a therapeutically effective amount of a combination of B vitamins and C vitamins. The constipation comprises functional constipation (caused by bad habits, dietary habits, senility, and other non-organic pathology) and drug-induced constipation. In one preferred embodiment, the composition comprising B vitamins and C vitamins is a composition comprising vitamin B1 (thiamine), vitamin B2 (riboflavin), vitamin B3 (niacin), vitamin B5 (pantothenic acid), vitamin B6, biotin, and vitamin C. In one more preferred embodiment, the composition comprising B vitamins and C vitamins is a composition comprising vitamin B1 (thiamine), vitamin B2 (riboflavin), vitamin B3 (niacin), vitamin B5 (pantothenic acid), vitamin B6, vitamin B12, folic acid, biotin, vitamin C, choline bitartrate, and inositol. In another more preferred embodiment, the composition comprising B vitamins and C vitamins is a composition comprising vitamin B1 (thiamine), vitamin B2 (riboflavin), vitamin B3 (niacin), vitamin B5 (pantothenic acid), vitamin B6, folic acid, biotin, vitamin C, choline bitartrate, inositol, and p-aminobenzoic acid.

In one embodiment, the promotion of gastrointestinal motility is used in a method for treatment of gastrointestinal dysfunction caused by or associated with surgery (such as the slowdown of intestinal peristalsis after operation) in an object in need thereof, the method comprising administering a therapeutically effective amount of a combination of B vitamins and C vitamins. In one preferred embodiment, the composition comprising B vitamins and C vitamins is a composition comprising vitamin B1 (thiamine), vitamin B2 (riboflavin), vitamin B3 (niacin), vitamin B5 (pantothenic acid), vitamin B6, biotin, and vitamin C. In one more preferred embodiment, the composition comprising B vitamins and C vitamins is a composition comprising vitamin B1 (thiamine), vitamin B2 (riboflavin), vitamin B3 (niacin), vitamin B5 (pantothenic acid), vitamin B6, folic acid, biotin, vitamin C, choline bitartrate, and inositol. In another more preferred embodiment, the composition comprising B vitamins and C vitamins is a composition comprising vitamin B1 (thiamine), vitamin B2 (riboflavin), vitamin B3 (niacin), vitamin B5 (pantothenic acid), vitamin B6, vitamin B12, folic acid, biotin, vitamin C, choline bitartrate, inositol, and p-aminobenzoic acid.

A preferred composition comprising B vitamins and C vitamins is a composition comprising vitamin B1 (thiamine), vitamin B2 (riboflavin), vitamin B3 (niacin), vitamin B5 (pantothenic acid), vitamin B6, biotin, and vitamin C. A more preferable composition comprising B vitamins and C vitamins is a composition comprising vitamin B1 (thiamine), vitamin B2 (riboflavin), vitamin B3 (niacin), vitamin B5 (pantothenic acid), vitamin B6, folic acid, biotin, vitamin C, choline bitartrate, and inositol. In another more preferred embodiment, the composition comprising B vitamins and C vitamins is a composition comprising vitamin B1 (thiamine), vitamin B2 (riboflavin), vitamin B3 (niacin), vitamin B5 (pantothenic acid), vitamin B6, vitamin B12, folic acid, biotin, vitamin C, choline bitartrate, and p-aminobenzoic acid.

The dosage form of the composition comprising B vitamins and C vitamins of the present invention can be, but not limited to a chewable tablet, various conventional adjuvants required for preparing different dosage forms can also be added to the composition of the present invention, such as disintegrants, lubricants, binders, antioxidants, complexing agents, and other pharmaceutical carriers to prepare by conventional preparation methods any of the commonly used oral dosage forms, such as dispersible tablets, granules, capsules, oral liquids, and other dosage forms.

The weight ratio of each component for the composition comprising B vitamins and C vitamins in the present invention can have a plurality of selections, and all of them have corresponding motility promotion effects on the gastrointestinal system. In certain embodiments, it can include the following components based on weight ratio: 5-10 parts of vitamin B1, 10-15 parts of vitamin B2, 6-25 parts of vitamin B3, 10-110 parts of vitamin B5, 5-10 parts of vitamin B6, 5-10 parts of biotin, 0.1-0.5 parts of folic acid, 0.001-0.3 parts of vitamin B12, 100-300 parts of choline bitartrate, and 50-500 parts of vitamin C. In one preferred embodiment, the combination of B vitamins comprises the following components based on weight ratio: 10 parts of vitamin B1, 15 parts of vitamin B2, 25 parts of vitamin B3, 110 parts of vitamin B5, 10 parts of vitamin B6, 9 parts of biotin, 0.4 parts of folic acid, 0.025 parts of vitamin B12, 250 parts of choline bitartrate, and 150 parts of vitamin C. In one more preferred embodiment, the combination of B vitamins comprises the following components based on weight ratio: 10 parts of vitamin B1, 15 parts of vitamin B2, 25 parts of vitamin B3, 110 parts of vitamin B5, 10 parts of vitamin B6, 9 parts of biotin, 0.4 parts of folic acid, 250 parts of choline bitartrate, 150 parts of vitamin C, and 250 parts of inositol. In another more preferred embodiment, the combination of B vitamins comprises the following components based on weight ratio: 10 parts of vitamin B1, 15 parts of vitamin B2, 25 parts of vitamin B3, 110 parts of vitamin B5, 10 parts of vitamin B6, 9 parts of biotin, 0.4 parts of folic acid, 250 parts of choline bitartrate, 150 parts of vitamin C, 250 parts of inositol, 0.025 parts of vitamin B12, and 50 parts of p-aminobenzoic acid.

Effects of various doses of 9 components of vitamin B and vitamin C and positive drugs on gastrointestinal transit rate of charcoal meal in mice with loperamide-induced constipation.

Figure 4:
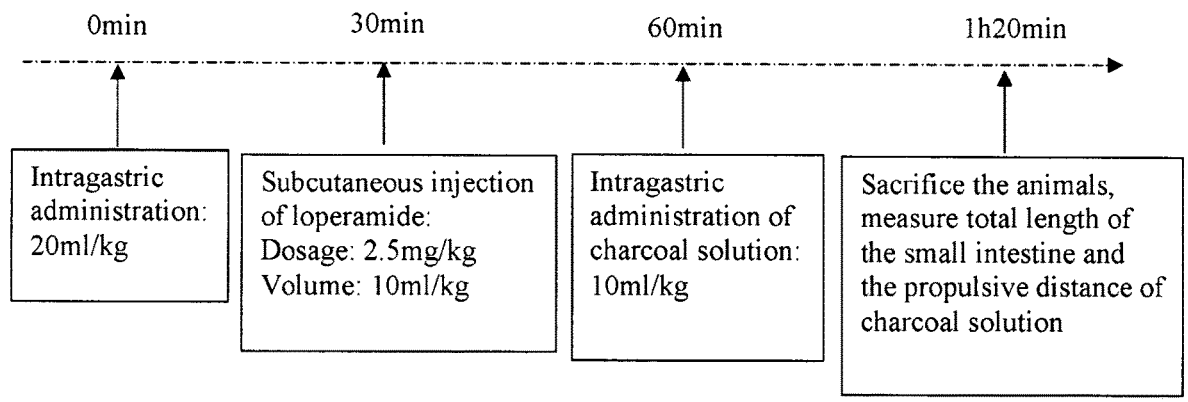

FIG. 4: a scheme of the test methods described in Section 2.3 of Example 1.

Figure 5:
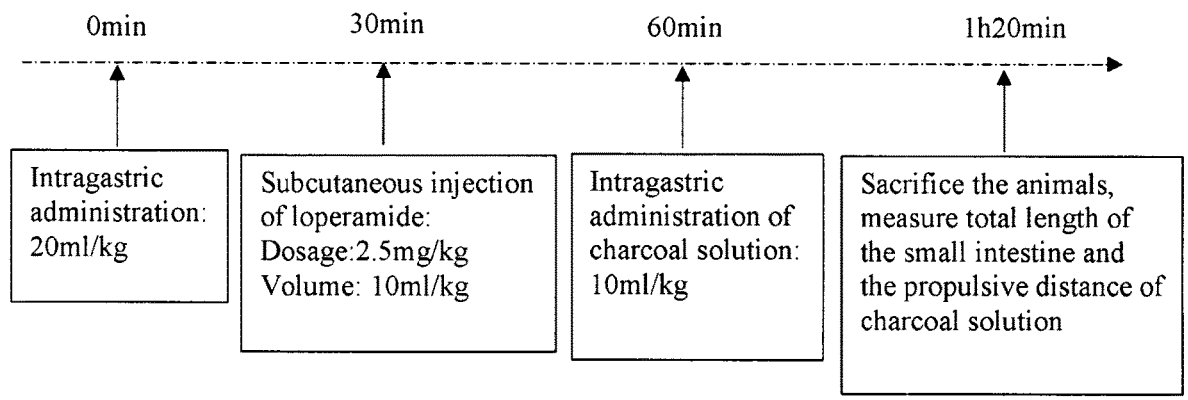

FIG. 5: a scheme of the test methods described in Section 2.3 of Example 2.

DETAILED DESCRIPTION

Example 1: Effects of the Composition Comprising B Vitamins (9 Components) and C Vitamins at Different Concentrations on the Small Intestinal Propulsive Rate in Mice with Loperamide-Induced Constipation 1 Experimental Materials
1.1 Drugs
A composition comprising B vitamins (9 components) and C vitamins
Manufacturer: ZENSUN (SHANGHAI) SCIENCE & TECHNOLOGY, CO. LTD.
Lot number: 2015.2.2
Purity: 100%
Character: yellow powder
Storage condition: being stored in a dry tank in darkness
1.2 Reagents and Instruments

| Reagents/instruments | Manufacturers | Lot/type |
|---|---|---|
| Loperamide | Sigma | 109K1107V |
| Arabic gum | Sinopharm Chemical | F20111122 |
| Carbon powder | Sinopharm Chemical | F20111213 |
| CMC-Na | Sinopharm Chemical | 20131022 |
| Tween 80 | Sinopharm Chemical | F20110615 |
| Saline solution | Qingzhou Yaowang Pharmaceutical Co., Ltd | 2F13091805 |
| Vitamin C tablet | Huazhong Pharmaceutical Co., Ltd | 20141049 |
| Analytical balance | Shanghai Balance Instrument Factory | JA8002 |

1.3 Experimental Animals
Species: mouse
Strains: C57BL/6
Gender and quantity: Female, 40
Animal week-age: 9 weeks
Weight range: 16.0-20.0 g
Animal sources: Shanghai Lingchang Biotechnology Co. LTD
Animal certificate number: 2013001803537
2. Experimental Design and Methods
2.1 Test Grouping:
Experimental animals were randomly divided into 5 groups (8 animals per group) by the random number table method. The specific grouping and administration doses are shown in Table 1 and Table 2.

TABLE 1

Doses for each group of mice

| Groups | Intragastric administration | Doses (mg/kg) | Subcutaneous injection |
|---|---|---|---|
| Model | 0.5% CMC-Na solution | — | Loperamide solution |
| VBs* + VC high dose | VBs* + VC high dose suspension | 1316.89 | Loperamide solution |
| VBs* + VC moderate dose | VBs* + VC moderate dose suspension | 438.96 | Loperamide solution |
| VBs* + VC low dose | VBs* + VC low dose suspension | 131.69 | Loperamide solution |
| Control | 0.5% CMC-Na solution | — | 1% Tween 80 in saline |

*VBs: B vitamins (9 components)

TABLE 2

Dose of each component of the multivitamin

| Combination of B vitamins | 9 components + VC Low dose group | 9 components + VC Moderate dose group | 9 components + VC High dose group |
|---|---|---|---|
| Vitamin B1 | 3.075 mg/kg | 10.25 mg/kg | 30.75 mg/kg |
| Vitamin B2 | 4.6125 mg/kg | 15.375 mg/kg | 46.125 mg/kg |
| Vitamin B3 | 7.6875 mg/kg | 25.625 mg/kg | 76.875 mg/kg |
| Vitamin B6 | 3.075 mg/kg | 10.25 mg/kg | 30.75 mg/kg |
| Calcium pantothenate | 33.426 mg/kg | 111.42 mg/kg | 334.26 mg/kg |
| Vitamin B12 | 7.688 ug/kg | 25.625 ug/kg | 76.875 ug/kg |
| Folic acid | 123 ug/kg | 410 ug/kg | 1230 ug/kg |
| Biotin | 2.808 mg/kg | 9.361 mg/kg | 28.08 mg/kg |
| Choline bitartrate | 76.875 mg/kg | 256.25 mg/kg | 768.75 mg/kg |
| Vitamin C | 153.75 mg/kg | 153.75 mg/kg | 153.75 mg/kg |

2.2 Reagent Preparation 1) 0.5% CMC—Na solution: 2.0 g of CMC—Na powder was weighed and 300 ml ultra-pure water was slowly added thereto; the mixture was subjected to magnetic stirring until it was completely dissolved to reach a constant volume of 400 ml, thereby preparing a clear solution of 0.5%, which was stored at 4° C. for later use.

2) 1% Tween-80 in saline: 40 ml saline was accurately measured using a measuring cylinder and added into a 50 ml centrifuge tube; 400 μl Tween-80 was measured using a pipette and added into the centrifuge tube; and the mixture was subjected to vortex oscillation to be homogeneous and was then placed at room temperature for later use.

3) 5% charcoal solution: 100 g of Arabic gum was accurately weighed and 800 ml water was added thereto; and the solution was boiled until it was transparent. 50 g of activated carbon powder was weighed and added into the above solution and the mixture was boiled for three times. After the solution was cool, water was added to reach a constant volume of 1000 ml.

4) High dose group for the composition comprising B vitamins (9 components) and C vitamins: 1.317 g of the combination of B vitamins (9 components) was accurately weighed and three VC tablets were added thereto; after grinding, 20 ml of 0.5% CMC—Na was added; and the mixture was subjected to oscillation to become homogeneous, thereby forming a stable suspension.

5) Moderate dose group for the composition comprising B vitamins (9 components) and C vitamins: 0.439 g of the combination of B vitamins (9 components) was accurately weighed and three VC tablets were added thereto; after grinding, 20 ml of 0.5% CMC—Na was added; and the mixture was subjected to oscillation to become homogeneous, thereby forming a stable suspension.

6) Low dose group for the composition comprising B vitamins (9 components) and C vitamins: 0.132 g of the combination of B vitamins (9 components) was accurately weighed and three VC tablets were added thereto; after grinding, 20 ml of 0.5% CMC—Na was added; and the mixture was subjected to oscillation to become homogeneous, thereby forming a stable suspension.

7) Loperamide: 5.0 mg of loperamide was accurately weighed and 20 ml of a saline solution with 1.0% Tween 80 was added thereto; after being subjected to oscillation to become homogeneous, the mixture was subjected to ultrasound for at least 5 minutes. This reagent was used immediately after it was prepared.

2.3 Test Methods

As illustrated in FIG. 4, after fasting and freely drinking for about 22-24 hours, each group of the mice were administrated at above doses at 20 ml/kg, and the model group and the control group were intragastrically administrated with 0.5% CMC—Na solution at the same dose. After 30 minutes of administration, the control group was injected subcutaneously with the saline solution containing 1.0% Tween 80 while the other groups were injected subcutaneously with loperamide in an injection volume of 10 ml/kg. After a subcutaneous injection for 30 minutes, an intragastric administration of the charcoal solution was performed at an administration volume of 10 ml/kg[1,2,3].

2.4 Observation Index

Small intestinal propulsive rate of the charcoal solution (%)=(the propulsive distance of the charcoal solution/total length of the small intestine)×100

Twenty minutes after an intragastric administration of the charcoal solution, the animal was sacrificed by cervical dislocation and its abdominal cavity was immediately opened to separate the mesentery. The intestinal canal from the pylorus to the ileocecal junction was carefully removed and put on a tray. Be careful not to involve the small intestine, gently place the small intestine in a straight line, and measure the total length of the small intestine. The length from the pylorus to the front of the charcoal solution is the propulsive distance of the charcoal solution, and the small intestinal propulsive rate (%) of the charcoal solution was calculated.

2.5 Data Analysis

Experimental data were expressed by X±S and one-way ANOVA was performed by SPSS. Comparison between groups was made using LSD test.

3 Test Results

Figure 1:
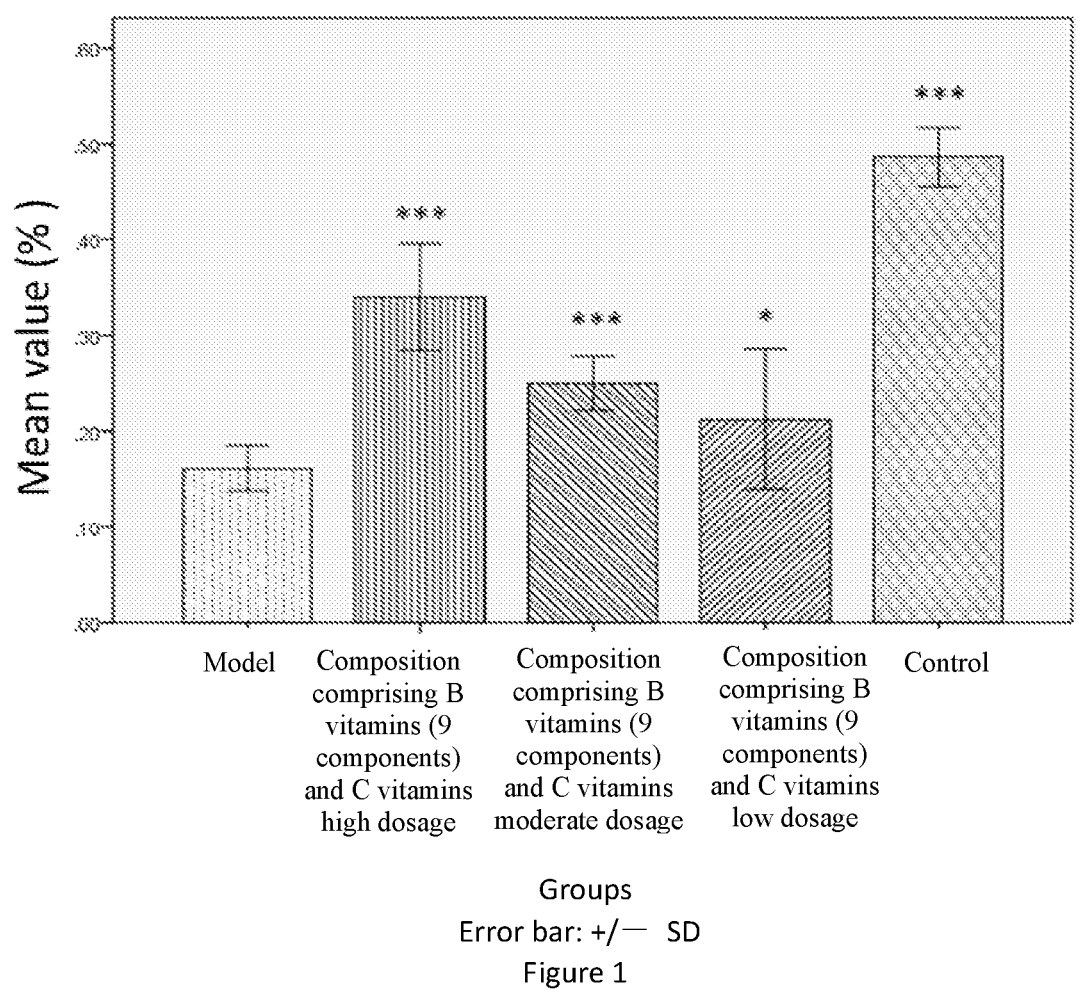
FIG. 1: effects of the composition comprising B vitamins (9 components) and C vitamins at different concentrations on the small intestinal propulsive rate (%) of a charcoal solution in mice with loperamide-induced constipation after administration in the first test.

Effects of the combination of B vitamins on the small intestinal propulsive distance and propulsive rate (%) of the charcoal solution in the mice in the first test are shown in Table 3 and FIG. 1 of the description.

Table 3: Effects of the composition comprising B vitamins (9 components) and C vitamins on the small intestinal propulsive rate in mice with loperamide-induced constipation in the first test (X±S)

| Groups | Animal number (n) | Animal weight (g) | Length of the small intestine (cm) | Propulsive distance of the charcoal solution (cm) | Small intestinal propulsive rate (%) |
|---|---|---|---|---|---|
| Model | 8 | 18.5 ± 0.7 | 19.0 ± 0.7 | 3.0 ± 0.5 | 16.1 ± 0.0 |
| VBs# + VC high dose | 8 | 18.3 ± 0.8 | 18.7 ± 0.9 | 6.4 ± 1.2*** | 34.0 ± 0.1*** |
| VBs# + VC moderate dose | 8 | 18.5 ± 0.6 | 18.5 ± 0.6 | 4.6 ± 0.5** | 25.0 ± 0.0*** |
| VBs# + VC low dose | 8 | 18.1 ± 0.6 | 19.2 ± 0.8 | 4.1 ± 1.4* | 21.3 ± 0.1* |
| control | 8 | 16.8 ± 0.2*** | 18.4 ± 0.4 | 8.9 ± 0.6*** | 48.6 ± 0.0*** |

*vs model group, $P < 0.05$;
**vs model group, $P < 0.01$;
VBs#: B vitamins (9 components)

The results of the first test showed that compared with the control group, the small intestinal propulsive rate (%) of the model group was significantly reduced (48.6±0.0 VS 16.1±0.0), indicating that the mouse constipation model was successfully prepared. Compared with model group, both the propulsive distance of the charcoal solution and the small intestinal propulsive rate thereof (%) were significantly increased in high, moderate and low dose groups ($p<0.05$). The improvement effect on the small intestinal propulsive rate (%) in mice is dose-dependent (34.0±0.1, 25.0±0.0 & 21.3±0.1 for high, moderate and low doses).

Figure 2:
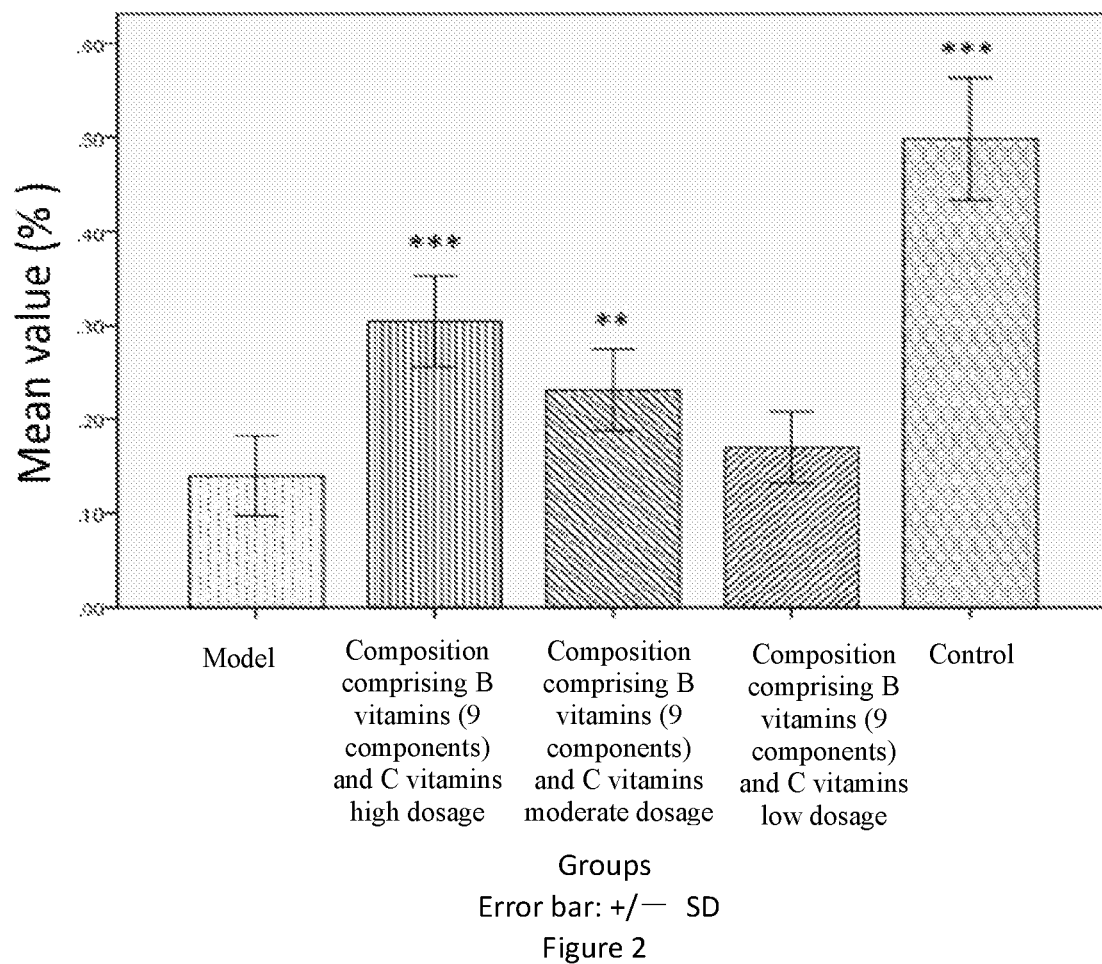
FIG. 2: effects of the composition comprising B vitamins (9 components) and C vitamins at different concentrations on the small intestinal propulsive rate (%) of a charcoal solution in mice with loperamide-induced constipation after administration in the repeated test.

Effects of the combination of B vitamins on the small intestinal propulsive distance and propulsive rate (%) of the charcoal solution in the mice in the repeated test are shown in Table 4 and FIG. 2 of the description. Table 4: Effects of the composition comprising B vitamins (9 components) and C vitamins on the small intestinal propulsive rate in mice with loperamide-induced constipation in the repeated test (X±S)

| Group | Animal number (n) | Animal weight(g) | Total length of the small intestine (cm) | Distance traveled by the activated carbon (cm) | Small intestinal propulsive rate (%) |
|---|---|---|---|---|---|
| Model | 8 | 17.9 ± 0.3 | 19.0 ± 0.9 | 2.6 ± 0.7 | 14.0 ± 0.0 |
| VBs# + VC high dose | 7 | 17.9 ± 0.4 | 18.9 ± 0.9 | 5.8 ± 1.1*** | 30.4 ± 0.0*** |
| VBs# + VC moderate dose | 6 | 17.8 ± 0.5 | 18.8 ± 0.9 | 4.3 ± 0.7** | 23.2 ± 0.0** |
| VBs# + VC low dose | 7 | 17.9 ± 0.4 | 19.3 ± 0.9 | 3.3 ± 0.6 | 17.0 ± 0.0 |
| control | 7 | 16.4 ± 0.5*** | 18.3 ± 1.2 | 9.0 ± 1.2*** | 49.9 ± 0.1*** |

*vs model group, $P < 0.05$;
**vs model group, $P < 0.01$;
VBs#: B vitamins (9 components)

The results of the repeated test showed that compared with the control group, the small intestinal propulsive rate (%) of the model group was significantly reduced (49.9±0.1 VS 14.0±0.0), indicating that the mouse constipation model was successfully prepared. Compared with model group, both the propulsive distance of the charcoal solution and the small intestinal propulsive rate thereof (%) were significantly increased in high, moderate and low dose groups ($p<0.05$). The improvement effect on the small intestinal propulsive rate (%) in mice is dose-dependent (30.4±0.0, 23.2±0.0 & 17.0±0.0 for high, moderate and low doses).

4. Conclusion

The high, moderate, and low dose groups of the test composition comprising B vitamins (9 components) and C vitamins can all significantly improve the small intestinal propulsive rate (%) in the loperamide-induced constipation mouse model and the improvement effect is dose-dependent for the high, moderate, and low dose groups.

Example 2: Effects of the Composition Comprising B Vitamins (9 Components) and C Vitamins and Positive Control on the Small Intestinal Propulsive Rate in Mice with 2.5 mg/kg Loperamide-Induced Constipation 1 Experimental Materials 1.1 Test Product A composition comprising B vitamins (9 components) and C vitamins Manufacturer: ZENSUN (SHANGHAI) SCIENCE & TECHNOLOGY, CO. LTD.

Lot number: 20150401

Purity: 100%

Character: yellow powder

Storage condition: being stored in a dry tank in darkness 1.2 Reagents and Instruments

| Reagents/instruments | Manufacturers | Lot/type |
|---|---|---|
| Arabic gum | Sinopharm Chemical | F20111122 |
| Carbon powder | Sinopharm Chemical | F20111213 |
| CMC-Na | Sinopharm Chemical | 20131022 |
| Tween 80 | Sinopharm Chemical | F20110615 |
| Saline | Qingzhou Yaowang Pharmaceutical Co., Ltd | 2F13091805 |
| Loperamide | Sigma | 109K1107V |
| Multivitamin BC tablet | Huazhong Pharmaceutical Co., Ltd | 20150401 |
| Domperidone | Xi'an-Janssen Pharmaceutical Ltd | 140325965 |
| Mosapride citrate capsules | Shanghai SINE Pharmaceutical Co., Ltd | 20141103 |
| Itopride hydrochloride | Xiuzheng Pharmaceutical | 140903 |

| Reagents/instruments | Manufacturers | Lot/type |
|---|---|---|
| tablets | Group | |
| Naloxone hydrochloride for injection | SINOPHARM Yixin Pharmaceutical Co.,Ltd | 1405021 |
| Analytical balance | Shanghai Balance Instrument Factory | JA8002 |

1.2 Experimental Animals
Species: mouse
Strains: C57BL/6
Gender and quantity: Female, 65
Animal week-age: 8-9 weeks
Weight range: 19.0-25.0 g
Animal sources: Shanghai Lingchang Biotechnology Co. LTD
Animal certificate number: 2013001804393
2. Experimental Design and Methods
2.1 Test Grouping:

Experimental animals were randomly divided into 8 groups (8 animals per group) by the random number table method. The specific grouping and administration doses are shown in Table 1 and Table 2.

TABLE 1

Doses for each group of mice

| Groups | Intragastric administration | Doses (mg/kg) | Subcutaneous injection |
|---|---|---|---|
| Model | 0.5% CMC-Na solution | — | Loperamide solution |
| VBs* + VC (5X) dose | VBs* + VC (5x) suspension | 592.714 | Loperamide solution |
| VBs* + VC (1X) dose | VBs* + VC (1X) suspension | 118.543 | Loperamide solution |
| Itopride | Itopride suspension | 30.75 | Loperamide solution |
| Naloxone | Naloxone solution | 5.0 | Loperamide solution |
| Domperidone | Domperidone suspension | 6.16 | Loperamide solution |
| Mosapride citrate | Mosapride Citrate suspension | 3.075 | Loperamide solution |
| Control | 0.5% CMC-Na solution | — | 1% Tween 80 in saline |

*VBs: B vitamins (9 components)

TABLE 2

Dose of each component of the multivitamin

| Number | Active Pharmaceutical Ingredients | Mg per tablet | Equivalent dose for mice * 5 |
|---|---|---|---|
| 1 | 1.095% Biotin | 9.13 | 9.361 |
| 2 | Vitamin B1 | 10 | 10.250 |
| 3 | Vitamin B2 | 15 | 15.375 |
| 4 | niacin | 25 | 25.625 |
| 5 | Vitamin B6 | 10 | 10.250 |
| 6 | Calcium pantothenate | 108.7 | 111.418 |
| 7 | Folic acid | 0.4 | 0.410 |
| 8 | Vitamin B12 | 0.025 | 0.026 |
| 9 | Choline Bitartrate | 250 | 256.250 |
| 10 | Vitamin C | 150 | 153.750 |
| | Total | 578.255 | 592.714 |

2.2 Reagent Preparation 1) 0.5% CMC—Na solution: 2.0 g of CMC—Na powder was weighed and 300 ml ultra-pure water was slowly added thereto; the mixture was subjected to magnetic stirring until it was completely dissolved to reach a constant volume of 400 ml, thereby preparing a clear solution of 0.5%, which was stored at 4° C. for later use.

2) 1% Tween-80 in saline: 40 ml saline was accurately measured using a measuring cylinder and added into a 50 ml centrifuge tube; 400 μl Tween-80 was measured using a pipette and added into the centrifuge tube; and the mixture was subjected to vortex oscillation to be homogeneous and was then placed at room temperature for later use.

3) 5% charcoal solution: 100 g of Arabic gum was accurately weighed and 800 ml water was added thereto; and the solution was boiled until it was transparent. 50 g of activated carbon powder was weighed and added into the above solution and the mixture was boiled for three times. After the solution was cool, water was added to reach a constant volume of 1000 ml.

4) Group for the composition comprising B vitamins (9 components) and C vitamins (5×): one tablet of the composition comprising B vitamins (9 components) and C vitamins was taken; after its grinding, 19.5 ml of 0.5% CMC—Na was added; and the mixture was subjected to oscillation to become homogeneous, thereby forming a stable suspension. It was used immediately after its preparation.

5) Group for the composition comprising B vitamins (9 components) and C vitamins (1×): 2 ml of the suspension of the composition comprising B vitamins (9 components) and C vitamins (5×) was taken and 8 ml of 0.5% CMC—Na was added; and the mixture was subjected to oscillation to become homogeneous, thereby forming a stable suspension. It was used immediately after its preparation.

6) Domperidone: 32.52 ml of 0.5% CMC—Na was added after grinding of one domperidone tablet; and the mixture was subjected to oscillation to become homogeneous, thereby forming a stable suspension. It was used immediately after its preparation.

7) Mosapride citrate: 32.52 ml of 0.5% CMC—Na was added after grinding of one mosapride citrate tablet; and the mixture was subjected to oscillation to become homogeneous, thereby forming a stable suspension. It was used immediately after its preparation.

8) Itopride hydrochloride: 32.52 ml of 0.5% CMC—Na was added after grinding of one itopride hydrochloride tablet; and the mixture was subjected to oscillation to become homogeneous, thereby forming a stable suspension. It was used immediately after its preparation.

9) Naloxone: 3.2 ml of 0.5% CMC—Na was added to one bottle of naloxone for injection (0.8 mg); and the mixture was subjected to oscillation to become homogeneous, thereby forming a clear solution. It was used immediately after its preparation.

10) Loperamide: 5.0 mg of loperamide was accurately weighed and 20 ml of a saline solution with 1.0% Tween 80 was added thereto; after being subjected to oscillation to become homogeneous, the mixture was subjected to ultrasound for at least 5 minutes. This reagent was used immediately after it was prepared.

2.3 Test Methods

As illustrated in FIG. 5, after fasting and freely drinking for about 22~24 hours, each group of the mice were administrated at above doses at 20 ml/kg, and the model group and the control group were intragastrically administrated with 0.5% CMC—Na solution at the same dose. After 30 minutes of administration, the control group was injected subcutaneously with the saline solution containing 1.0% Tween 80 while the other groups were injected subcutaneously with a loperamide solution in an injection volume of 10 ml/kg. After a subcutaneous injection for 30 minutes, an intragastric administration of the charcoal solution was performed at an administration volume of 10 ml/kg[1,2,3].

2.4 Observation Index

Small intestinal propulsive rate of the charcoal solution (%)=(the propulsive distance of the charcoal solution/total length of the small intestine)×100

Twenty minutes after an intragastric administration of the charcoal solution, the animal was sacrificed by cervical dislocation and its abdominal cavity was immediately opened to separate the mesentery. The intestinal canal from the pylorus to the ileocecal junction was carefully removed and put on a tray. Be careful not to involve the small intestine, gently place the small intestine in a straight line, and measure the total length of the small intestine. The length from the pylorus to the front of the charcoal solution is the propulsive distance of the charcoal solution, and the small intestinal propulsive rate (%) of the charcoal solution was calculated.

2.5 Data Analysis

Experimental data were expressed by X±S and one-way ANOVA was performed by SPSS. Comparison between groups was made using LSD test.

3 Test Results

Figure 3:
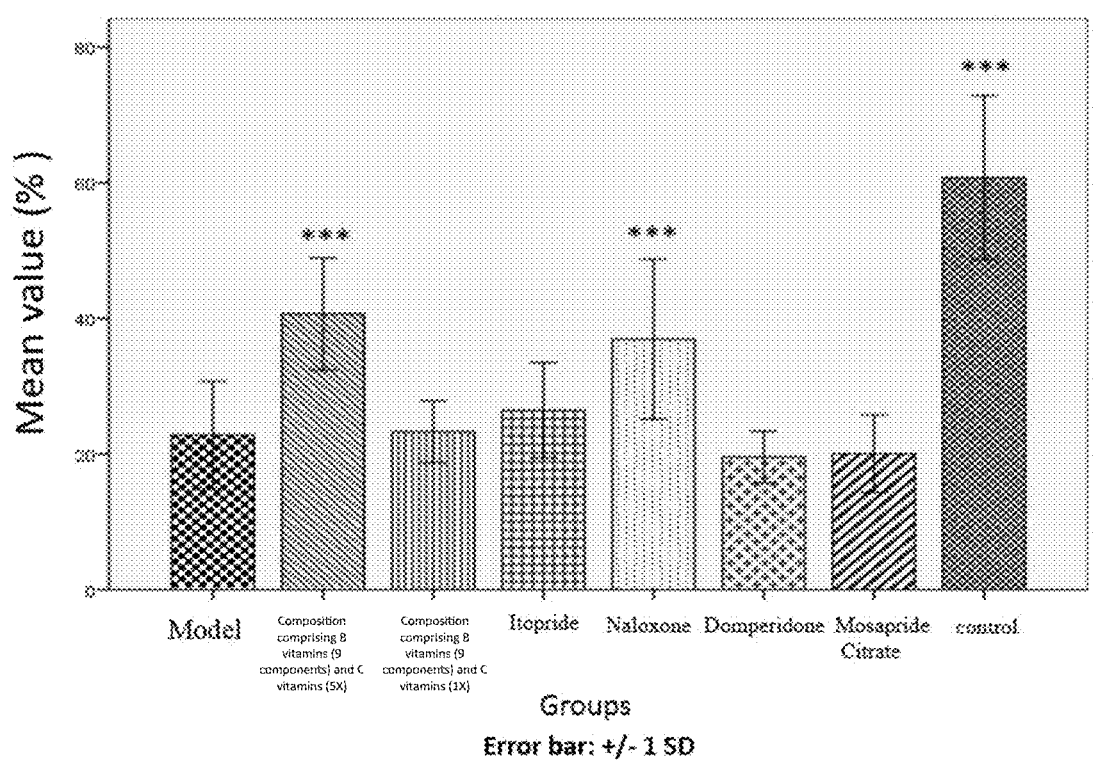
FIG. 3: effects of the composition comprising B vitamins (9 components) and C vitamins and positive control on the small intestinal propulsive rate (%) of a charcoal solution in mice with 2.5 mg/kg loperamide-induced constipation after administration.

Effects of the combination of B vitamins on the small intestinal propulsive distance and propulsive rate (%) of the charcoal solution in the mice are shown in Table 3 and FIG. 3 of the description.

The results of the test showed that compared with the control group, the small intestinal propulsive rate (%) of the model group was significantly reduced (60.7±12.1 VS 22.8±7.9), indicating that the mouse constipation model was successfully prepared. Compared with the model group, the improvement effect on small intestinal propulsive rate (%) is dose-dependent for the VBs*+VC (5×) tablet group, Naloxone group, and the control group (40.6±8.3, 36.9±11.8 & 60.7±12.1), the three positive drugs including itopride hydrochloride, mosapride citrate and domperidone cannot obviously improve the small intestinal propulsive rate at 1× dose (26.4±7.0, 20.1±5.7 & 19.5±3.8).

4. Conclusion

The test composition comprising B vitamins (9 components) and C vitamins (5×) can all significantly improve the small intestinal propulsive rate (%) in the loperamide-induced constipation mouse model, and the positive drug naloxone also has the improvement effect. Three other positive drugs including itopride hydrochloride, mosapride citrate, and domperidone do not have the improvement effect.

In order to more clearly describe and understand this invention, we have described this invention in detail by way of examples, but it is obvious that those of ordinary skill in the art can make the appropriate changes or modifications to this invention without departing from the spirit and scope of the claims.

What is claimed is:

1. A method for treating a condition or disease associated with insufficient gastrointestinal system motility in a subject in need thereof, comprising administering a composition comprising B vitamins and C vitamins to the subject, wherein the composition comprising B vitamins and C vitamins comprises the following components based on weight ratio: 10 parts of vitamin B1, 15 parts of vitamin B2, 25 parts of vitamin B3, 110 parts of vitamin B5, 10 parts of vitamin B6, 0.1 parts of vitamin B7, 0.4 parts of vitamin B9, 0.025 parts of vitamin B12 and 150 parts of vitamin C.

2. The method of claim 1, wherein the composition comprising B vitamins and C vitamins comprises a combination of B vitamins or analogue or derivatives thereof and vitamin C or analogues or derivative thereof.

3. The method of claim 2, wherein the vitamin B1 is thiamine, the vitamin B2 is riboflavin, the vitamin B3 is niacin, the vitamin B5 is pantothenic acid, the vitamin B7 is biotin, and the vitamin B9 is folic acid.

TABLE 3

Effects of the composition comprising B vitamins (9 components) and C vitamins and positive control on the small intestinal propulsive rate in mice with loperamide-induced constipation (X ± S)

| Groups | Animal number (n) | weight (g) | Length of the small intestine (cm) | Propulsive distance of the charcoal solution (cm) | Small intestinal propulsive rate (%) |
|---|---|---|---|---|---|
| model | 10 | 22.0 ± 1.4 | 20.5 ± 1.6 | 4.7 ± 1.7 | 22.8 ± 7.9 |
| VBs* + VC (5X) moderate dose group | 10 | 22.7 ± 0.8 | 19.3 ± 1.4* | 7.8 ± 1.7*** | 40.6 ± 8.3*** |
| VBs* + VC (1X) low dose group | 7 | 22.3 ± 1.0 | 19.1 ± 1.1* | 4.4 ± 0.8 | 23.3 ± 4.6 |
| Itopride hydrochloride | 8 | 22.5 ± 1.1 | 19.1 ± 1.1* | 5.0 ± 1.2 | 26.4 ± 7.0 |
| Naloxone | 8 | 22.6 ± 1.0 | 18.5 ± 1.4*** | 6.8 ± 1.9** | 36.9 ± 11.8*** |
| Domperidone | 7 | 22.4 ± 0.6 | 20.0 ± 0.9 | 3.9 ± 0.8 | 19.5 ± 3.8 |
| Mosapride Citrate | 8 | 21.8 ± 1.0 | 20.2 ± 0.7* | 4.0 ± 1.1 | 20.1 ± 5.7 |
| control | 7 | 21.8 ± 1.7 | 19.3 ± 0.5 | 11.7 ± 2.1*** | 60.7 ± 12.1*** |

Compared with the model group, *P < 0.05, P < 0.01, *P < 0.001

4. The method of claim 2, wherein the vitamin C or analogues or derivatives thereof are selected from L-ascorbic acid, L-sodium ascorbate, magnesium ascorbyl phosphate, L-Ascorbate-polyphosphate, ascorbyl palmitate, ascorbin stearate, and vitamin C and glucose compound.

5. The method of claim 2, wherein the composition comprising B vitamins and C vitamins further comprises Choline Bitartrate.

6. The method of claim 5, wherein the Choline Bitartrate is 250 parts in weight ratio.

7. The method of any one of claim 5, wherein the composition comprising B vitamins and C vitamins further comprises inositol and p-aminobenzoic acid.

8. The method of any one of claim 2, wherein the composition comprising B vitamins and C vitamins further comprises inositol and p-aminobenzoic acid.

9. The method of claim 1, wherein the composition comprising B vitamins and C vitamins further comprises Choline Bitartrate.

10. The method of claim 9, wherein the Choline Bitartrate is 250 parts in weight ratio.

11. The method of any one of claim 9, wherein the composition comprising B vitamins and C vitamins further comprises inositol and p-aminobenzoic acid.

12. The method of any one of claim 1, wherein the composition comprising B vitamins and C vitamins further comprises inositol and p-aminobenzoic acid.

\* \* \* \* \*